United States Patent
Fisher (10) Patent No.: US 6,171,259 B1
(45) Date of Patent: Jan. 9, 2001

(54) FECAL SPECIMEN SAMPLING AND ANALYSIS

(76) Inventor: David W. Fisher, P.O. Box 5794, Texarkana, TX (US) 75505

(*) Notice: Under 35 U.S.C. 154(b), the term of this patent shall be extended for 0 days.

(21) Appl. No.: 08/158,519

(22) Filed: Nov. 29, 1993

Related U.S. Application Data (63) Continuation-in-part of application No. 07/844,619, filed on Mar. 27, 1992, now Pat. No. 5,265,620, which is a continuation-in-part of application No. PCT/US90/04414, filed on Aug. 7, 1990, which is a continuation-in-part of application No. 07/487,928, filed on Mar. 5, 1990, now abandoned, which is a continuation-in-part of application No. 07/390,602, filed on Aug. 7, 1989, now abandoned.

(51) Int. Cl.$^7$ .................................................... A61B 5/00
(52) U.S. Cl. .......................................... 600/549; 600/562
(58) Field of Search ............................... 128/736, 749, 128/751, 753, 754, 756, 757; 600/549, 562, 564, 566, 567, 569, 570, 572

(56) References Cited

U.S. PATENT DOCUMENTS

| | | |
|---|---|---|
| 738,960 | 9/1903 | Vaughn . |
| 2,969,141 | 1/1961 | Katzin . |
| 3,190,436 | 6/1965 | Diamant . |
| 3,640,268 * | 2/1972 | Davis ............................... 128/757 X |
| 3,650,153 | 3/1972 | Schwab . |
| 3,783,998 | 1/1974 | Brush et al. . |
| 3,800,781 | 4/1974 | Zalucki . |
| 3,822,593 | 7/1974 | Oudewaal . |
| 3,826,259 | 7/1974 | Bailey . |
| 3,857,384 * | 12/1974 | Watson .................................. 128/749 |
| 4,197,944 | 4/1980 | Catlin . |
| 4,263,921 | 4/1981 | Trugillo . |
| 4,312,950 | 1/1982 | Snyder et al. . |
| 4,351,616 | 9/1982 | Farnstrom et al. . |
| 4,476,872 * | 10/1984 | Perlin ............................... 128/736 X |
| 4,562,043 | 12/1985 | Mennen et al. . |
| 4,707,450 | 11/1987 | Nason . |
| 4,862,899 * | 9/1989 | Bucaro ................................. 128/749 |
| 5,031,635 * | 7/1991 | Koll ..................................... 128/756 |
| 5,269,316 * | 12/1993 | Spitalny ............................ 128/751 X |

* cited by examiner

*Primary Examiner*—Sam Rimell
(74) *Attorney, Agent, or Firm*—Daniel N. Lundeen (57) ABSTRACT

The present invention discloses a device, kit and method for concurrent sampling of a fecal specimen and temperature measurement from a single rectal penetration. The device comprises an elongated, rigid, cylindrical sleeve with a partially cutaway distal end to form a scoop and a thermometer optionally inserted into a bore in the sleeve. The kit includes, in addition to the sleeve, a vial adapted to receive the sleeve therein for permitting analysis of the fecal specimen in the sampling scoop in the vial by enclosure thereof with the vial for containment of an analyzing solution in contact with the fecal specimen. The method includes inserting the sleeve into the rectum, obtaining a fecal specimen in the scoop, optionally measuring the rectal temperature, withdrawing the sleeve, securing the scoop end of the sleeve in the vial, and contacting the fecal specimen from the scoop with an analysis solution contained in the vial.

17 Claims, 7 Drawing Sheets

FIG. 25

# FECAL SPECIMEN SAMPLING AND ANALYSIS

CROSS-REFERENCE TO RELATED APPLICATIONS

This application is a continuation-in-part of my earlier application U.S. Ser. No. 07/844,619, filed Mar. 27, 1992, now U.S. Pat, No. 5,265,620, which was a continuation-in-part of my earlier copending application PCT/US90/04414, filed Aug. 7, 1990, which was a continuation-in-part of my earlier copending application U.S. Ser. No. 07/487,928, filed Mar. 5, 1990, abandoned, which was a continuation-in-part of my earlier application U.S. Ser. No. 07/390,602, filed Aug. 7, 1989, abandoned.

FIELD OF THE INVENTION

This invention relates to a fecal specimen sampling device and more particularly to a fecal specimen sampling device having analyzing and temperature measuring elements.

BACKGROUND OF THE INVENTION

The medical care field has increasingly moved towards the use of disposable implements for conducting routine invasive testing because of the increased availability of new inexpensive plastic materials and an awareness of the difficulty and high cost of sterilizing reusable equipment.

Disposable medical implements are not, however, totally free of problems because disposability means increased supply costs and much more waste being produced. Medical waste is typically more expensive to dispose of than ordinary waste.

Medical practice upon certain patients such as children (or dogs and cats in the case of veterinary practice) can be more difficult due to uncooperativeness of the patient. It would be beneficial to adopt shortcuts in testing procedures where feasible to limit patient discomfort.

It is also desirable that the pathology of biological specimens be evaluated within the container in which the specimen is obtained and/or transported. This eliminates the need for additional transferring steps. Pathology evaluations can thus be undertaken in a less costly and waste-producing fashion which is quick, convenient, and safe.

There are various temperature-taking implements and feces sampling devices having a variety of special features in the prior art. Applicant, however, is not aware of such separate use implements having been previously combined to enable a medical practitioner to both take the temperature and remove a specimen of feces from a patient by means of a single rectal penetration, wherein the feces specimen can then promptly be evaluated within the sampling implement.

U.S. Pat. No. 3,822,593 to Oudewaal discloses a clinical thermometer probe with a disposable cover. The probe is made of a cylindrical tube with a thermistor probe contained in the hollow interior. A disposable cover with a membrane terminus engages the tube at the temperature sensing end.

U.S. Pat. No. 4,263,921 to Trugillo discloses a temperature sensing endotracheal tube. A thermistor is mounted on the distal end portion through the side wall of the tube.

U.S. Pat. No. 4,312,950 to Snyder et al. discloses a disposable swab and culture unit made of a two-piece telescoping plastic cylinder which forms a disposable container for the swab and a liquid culture medium.

U.S. Pat. No. 4,707,450 to Nason discloses a specimen collection and test unit which has a fibrous swab tip at one end of an elongated hollow shank for use in collecting biological specimens. Test reagents can be pumped through the shank to the swab tip.

U.S. Pat. No. 3,826,259 to Bailey discloses a self-contained disposable swab-type medication applicator with an encapsulated topical medicine. The medicine is released by squeezing the capsule and a cover material is removed to expose the medicated swab.

U.S. Pat. No. 2,969,141 to Katzin discloses a disposable plastic cover for a thermometer.

U.S. Pat. No. 4,562,043 to Mennen et al. discloses a tubular test device for testing occult blood in fecal matter using hydrogen peroxide in an ampoule adjacent a swab.

Other U.S. Patents of interest include No. 3,190,436 to Diamant; No. 738,960 to Vaughan; No. 4,351,616 to Farnstrom et al.; No. 4,297,944 to Catlin; No. 3,800,781 to Zalucki; No. 3,783,998 to Brush et al.; and No. 3,650,153 to Schwab.

SUMMARY OF THE INVENTION

A combination thermometer and fecal specimen sampling device permits the concurrent sampling of a fecal specimen and the measuring of body temperature from a single penetration of the rectum. Furthermore, a fecal specimen analyzing means is provided for performing a quick and simple on-the-spot analysis of the fecal specimen, or preserving means for maintaining integrity of the fecal specimen for later laboratory work.

In one embodiment, the present invention provides a device for simultaneously sampling a fecal specimen and measuring rectal temperature. The device comprises a rigid and elongated disposable tubular sleeve having open proximal and distal ends, the distal end having rounded edges adapted for rectal insertion and at least partially cut away longitudinally and transversely to form an open-ended scoop for collecting and containing a fecal specimen from the rectum. An interior bore is formed throughout the sleeve and a temperature measuring device is removeably inserted in the bore so that a temperature sensing end is thermally exposed adjacent the scoop. The temperature sensing end concurrently measures body temperature while the fecal specimen is obtained. A securing means inhibits longitudinal sliding of the temperature measuring device in the bore. An enclosure is sealably secured around the scoop after rectal insertion to contact the fecal specimen in the scoop with an analyzing solution contained by the enclosure.

In a preferred embodiment, the enclosure comprises a vial having an interior seat sealably locking with an exterior surface of the disposable tubular sleeve. The enclosure can also comprise a cap suitable for sealing the scoop end of the sleeve. The sleeve can further include a score or weakened section formed thereon for cleaving the proximal end from the distal end lodged in the vial. The device can further comprise a mixing rod inserted in the interior bore for mixing the fecal specimen with the analyzing solution.

In another embodiment, the present invention provides a method for sampling a fecal specimen and measuring rectal temperature. The method includes inserting the device as described above into the rectum; sampling the fecal specimen; measuring the temperature; and withdrawing the device from the rectum.

In a preferred embodiment, the method also includes steps for analyzing the fecal specimen. The analyzing steps can include: removing the thermometer from the sleeve; contacting the fecal specimen in the scoop with an analyzing solution; and reading a test result. The contacting step preferably comprises enclosing the scoop in a test tube and mixing the fecal specimen and analyzing solution using a mixing rod inserted in the interior bore.

As another aspect, a complete kit is provided for rectal insertion, fecal sampling, and fecal analysis including the sleeve and vial as mentioned above, and optionally including a thermometer or thermistor, a stirring rod, a hand-held appliance for mechanically rotating the stirring rod, and/or various reagents and solvents for analysis or preservation of the fecal specimen.

DESCRIPTION OF THE PREFERRED EMBODIMENT

Figure 1:
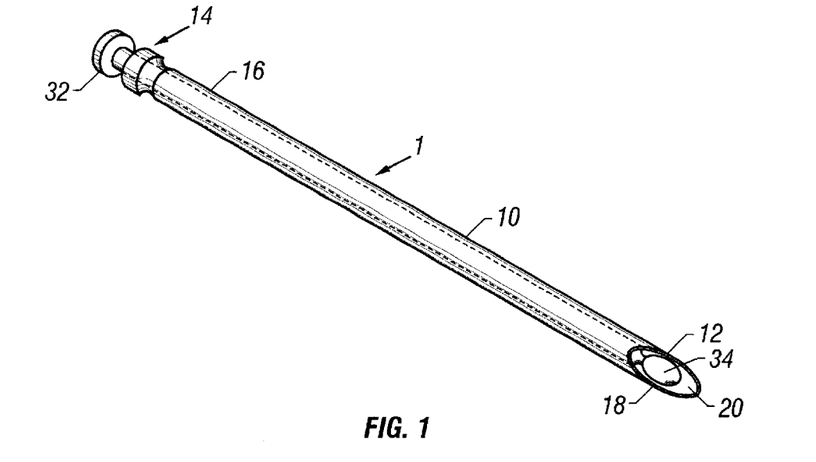
FIG. 1 is a perspective view of the sleeve and thermometer, partially in phantom, of one embodiment according to the present invention.

Referring to the drawings in which like reference numerals indicate like parts and features, in FIG. 1, there is shown a combined fecal specimen sampling and temperature measuring device 1 which includes a fecal specimen sampling sleeve 10.

Figure 2:
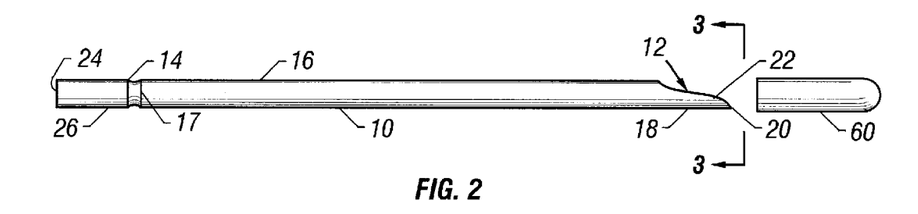
FIG. 2 is a side elevation of the sleeve and cap of one embodiment according to the present invention.

The sleeve 10, also seen in FIG. 2, has an interior bore 24 and cylindrical wall 16 with a diameter suitable for insertion into the rectum. The sleeve 10 preferably comprises a cylindrical, elongated and substantially rigid tube. The bore 24 includes a thermometer 30 or a plunger 40 inserted therein. The sleeve 10 is designed so that the interiorly inserted thermometer 30 is removably secured and inhibited from sliding in the sleeve 10, but can be easily inserted before use and withdrawn after use, and yet the plunger 40 can easily slide therein.

The sleeve 10 has a proximal end 14 and distal end 12. In the embodiment illustrated in FIG. 2, a shoulder 17 at the proximal end 14 extends radially inwardly narrowing the diameter of the bore 24. An annular groove 23 corresponding to the shoulder 17 is cut radially inwardly into the thermometer 30. The shoulder 17 and the groove 23 provide one preferred means for inhibiting sliding of a thermometer 30 in the sleeve 10.

Figure 9:
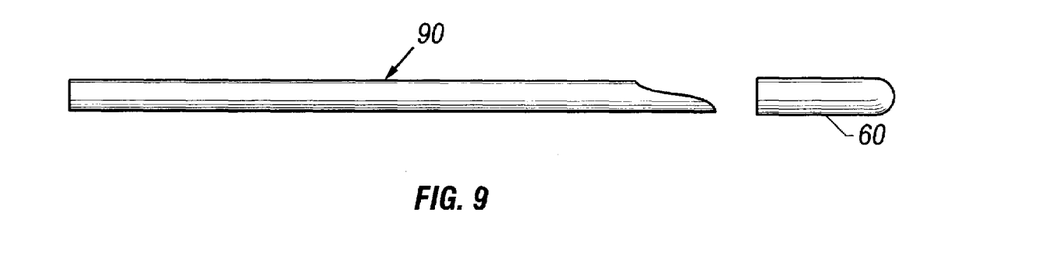
FIG. 9 is a side elevation of an alternate sleeve of the present invention without an inwardly radially extending shoulder.

In another embodiment illustrated in FIG. 9, a sleeve 90 has no shoulder 17 and the preferred slide inhibiting means is provided by the bore 24 which has a diameter closely dimensioned to a diameter of the thermometer 70. In a preferred embodiment, the bore 24 is slightly out of round, or of oval transverse cross-section to removably secure a thermometer inserted therein, wherein the thermometer 70 has, for example, a triangular transverse cross-section to tightly engage at the small-diameter surfaces of the bore 24, or release therefrom for removal of the thermometer 70 from the bore 24 by suitable rotation of the thermometer 70.

Figure 8:
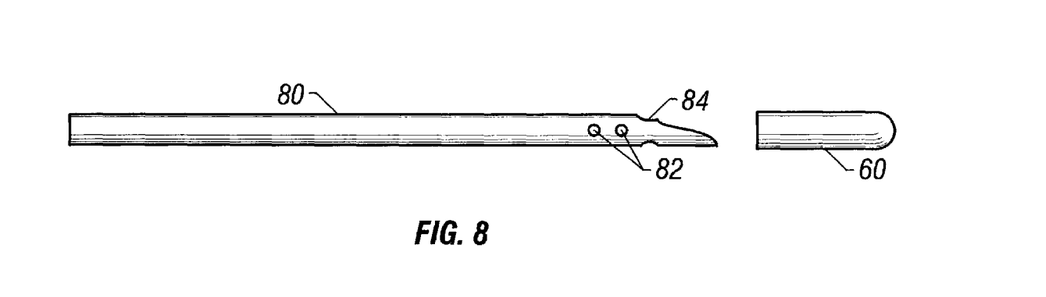
FIG. 8 is a side elevation of an alternate sleeve of the present invention having an inwardly radially extending shoulder at a distal end and vent holes.

In a further embodiment illustrated in FIG. 8, a distal end shoulder 84 of the sleeve 80 extends radially inwardly. The shoulder 84 is suitable for receiving a groove 72 on the thermometer 70 to inhibit free sliding of the thermometer 70 in the sleeve 80.

Figure 10:
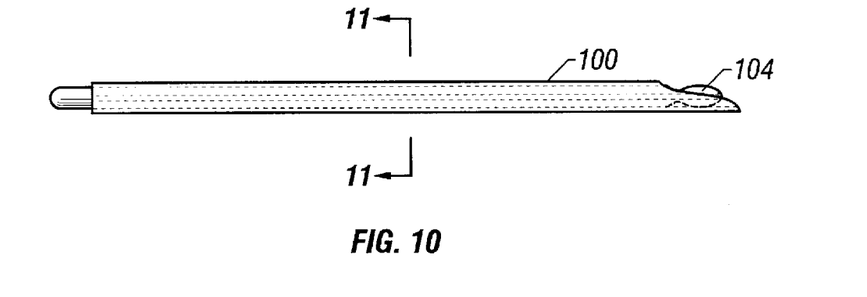
FIG. 10 is a side elevation of an alternate sleeve of the present invention having longitudinal fins along the walls of the bore.
Figure 11:
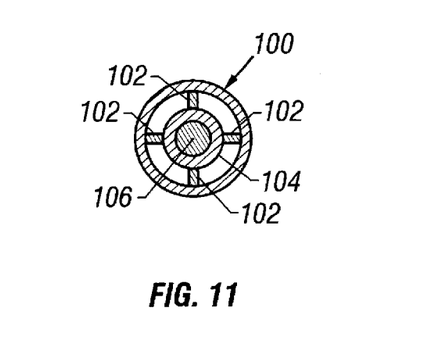
FIG. 11 is a cross-sectional of the sleeve of FIG. 10 along the lines 11—11.

In yet a further embodiment illustrated in FIGS. 10–11, a sleeve 100 is provided with a plurality of radially distributed longitudinal fins 102 projecting inwardly into the interior walls of bore 24. The fins 102 engage the outside surface of a thermometer 104 (having, for example, a mercury core 106) to removably secure the thermometer 104 inserted therein. The fins 102 have, for example, dimensions of about 0.25 mm width and about 0.38 mm length. Other removably securing means known in the art may also be suitable.

Figure 3:
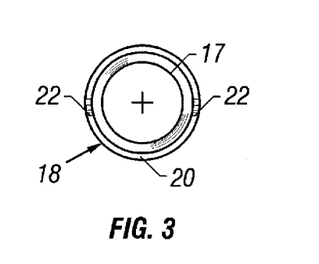
FIG. 3 is a cross-sectional view of the sleeve taken along the lines 3—3 of FIG. 2.

At an open distal end 12 of sleeve 10, the cylinder wall 16 is partially cut away longitudinally and transversely to form a scoop 20. The scoop 20 preferably comprises a partial cylinder wall 18 having an arc of about 180° as best seen in FIGS. 1, 2 and 3. The scoop 20 preferably has rounded sides 22 to smooth out rough edges and sharp points to minimize contusions or lacerations from insertion of the sleeve 10 into the rectum.

The sleeves 10, 80 or 90 can include one or more vent holes 82 (see FIG. 8) to allow air to escape from the sleeve when a cap 60 is used to cover the sleeve and the plunger 40 is inserted therein.

The sleeve 10 can be manufactured from a thermoplastic material exemplified by polyacrylics, e.g. acrylic-Br, polycarbonates, polyolefins, e.g. polyethylene and polypropylene, and the like; metallic material such as aluminum, stainless steel, and the like; or glass.

Figure 4:
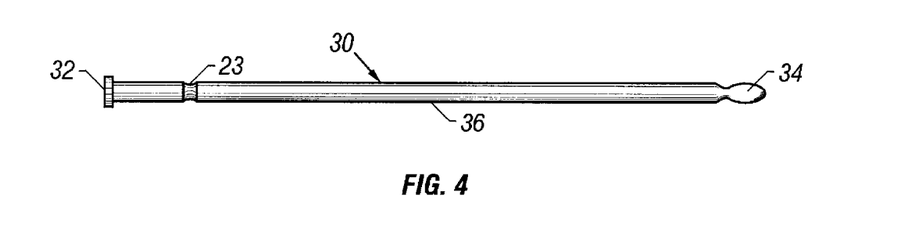
FIG. 4 is a side elevation view of a thermometer in an embodiment of the present invention.

When device 1 is utilized to measure temperature and obtain a fecal specimen, the thermometer 30 or other temperature measuring implement is inserted into the central bore 24 of sleeve 10. In one embodiment shown in FIG. 4, the thermometer 30 has a bulbous distal end 34 and a proximal flange end 36 wider in diameter than the bore 24. The flange 32 facilitates withdrawal of the thermometer 30. In another embodiment shown in FIG. 7, the thermometer 70, well known in the art as a rectal thermometer, has a bulbous distal end 34 which defines the groove 72 but no flange end.

Figure 7:
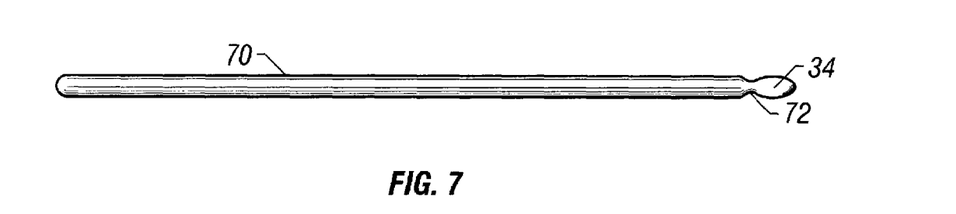
FIG. 7 is a side elevation of a thermometer in an embodiment of the present invention.

In a preferred embodiment, the sleeve 90 is manufactured by extrusion as an elongated, rigid tube. For use with a CORNELL thermometer, for example, the outside diameter is nominally 6.5 mm and the bore diameter is 4.95 mm; the cut-away scoop 20 has a nominally 19 mm length and the overall sleeve length is nominally 10.2 cm. These dimensions can, of course, be varied for use with other conventional thermometers. The off-the-shelf rectal thermometer 70, as seen in FIG. 7, is removably secured in the interior bore 24 so that the temperature sensing end 34 is adjacent the distal sleeve end scoop 20. The overall length of the sleeve is preferably shorter than the inserted thermometer 70 and the plunger 40. The length of the scoop 20 is sufficient to provide adequate volume in the scoop end to hold the fecal specimen.

Figure 5:
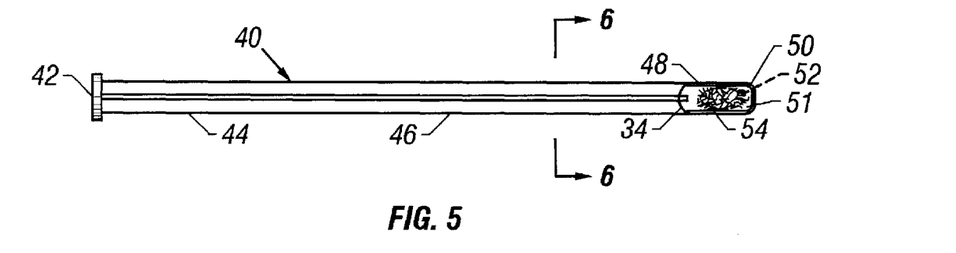
FIG. 5 is a side elevation of a plunger in accordance with one embodiment of the present invention.
Figure 6:
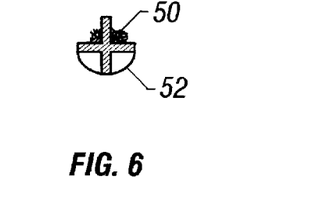
FIG. 6 is a cross-sectional view taken along lines 6—6 of FIG. 5.

In another embodiment of the present invention, the interior bore 24 of the fecal specimen sampling sleeve 10 has a cylindrical shaped plunger 40 inserted therein. The plunger 40 has a fecal specimen analyzing means 51 disposed at a distal end 48. As seen in FIGS. 5 and 6, the plunger 40 also has a proximal end flange 42 wider in diameter than the bore 24. The flange 42 facilitates insertion and withdrawal of the plunger 40 into and from the sleeve 10. The distal end 48 of the plunger 40 has mounting surface 50 for holding the analyzing means 51. The analyzing means 51 is suitable for performing tests on the fecal specimen sample obtained by the sleeve 10. The analyzing means 51 generally comprises a blanket or gauze member 54 wetted by liquid, such as, for example, cotton or another fiber wetted by an analyzing solution. The solution can be absorbed on the fibers, or contained in a frangible ampoule 52 embedded therein. Examples of such tests include a Guaiac test for occult blood, analysis for the presence of microorganisms such as yeast, viruses, rickettsia, bacteria and parasites, preparation for staining, and the like well known in the art. When the frangible ampoule 52 contains the Guaiac test fluid, the analyzing fluid typically comprises a weak hydrogen peroxide solution in ethanol. The ampoule 52 can also contain an enrichment broth such as nutrient agar for culturing. Prior to microscopic examination for parasites and/or parasite eggs, the ampoule 52 can contain a preservation fluid. Examples of preservatives include polyvinyl alcohol, isopropyl alcohol, buffered glycerol, saline and formalin. Staining can also be effected by using a stain in the ampoule 52. An ordinary practitioner in the art will be familiar with these and other tests which can be conducted on fecal specimens and appropriate reagents utilized therefor which can be contained in the frangible ampoule 52.

In the practice of the present invention, when a medical or veterinary practitioner desires to sample a fecal specimen, a sufficient length of the fecal specimen sampling device 1 is inserted into the rectum to gently sample a fecal specimen within the distal scoop 20. The device 1 may have to be gently swiveled and/or pivoted in order to withdraw a sufficiently large specimen for the desired fecal analysis. The thermometer is read and removed from the sleeve. The specimen contained in the scoop 20 is covered with the cap or vial 60 to prevent outside contact with the sample and exterior surfaces of the sleeve 10 that have penetrated the rectum. The cap 60 typically has an inside diameter closely matching the outside diameter of sleeve 10 so that the cap 60 covering the sleeve 10 is firmly engaged. The sample can then be analyzed by the analyzing means and/or sent to a laboratory for analysis.

When it is desired to conduct a quick single-step test on the fecal specimen contained in the sleeve 10, either with or without an earlier temperature measurement with the device 1, the plunger 40 can be used to bring the analyzing reagents in the cupped region 50 on plunger 40 into contact with the fecal specimen in the scoop 20 of sleeve 10. In this manner, the fecal specimen may be quickly analyzed without the need of sending the specimen to a laboratory for analysis. The analyzing reagents in frangible ampoule 52 are released, typically, by breaking the ampoule 52 under hand pressure. Generally, the sleeve 10 is covered by the cap 60 and the plunger 40 is inserted into the bore 24 of sleeve 10 until the analyzing reagents are in contact with the fecal specimen in the distal scoop 20. The cap 60 minimizes loss of analyzing solution and facilitates good contact with the specimen. The plunger 40 is withdrawn and analysis is typically indicated by color change in the blanket 54 soaked with the analyzing reagents in contact with the fecal specimen. Both plunger and sleeve can be conveniently disposed of, or the capped sleeve can be sent to a lab for further analysis.

When it is desired to simultaneously measure rectal temperature and take a fecal specimen, the device 1 of the present invention includes the temperature measuring implement inserted into the bore 24 of sleeve 10. To obtain an accurate temperature reading, the thermometer 30, for example, should be inserted into the sleeve 10 so that the temperature sensing bulbous end 34 resides in the distal scoop end 12 of sleeve 10. Device 1 is then inserted into the rectum for a period of time sufficient to obtain an accurate temperature measurement. Following the sampling procedures mentioned above, the device 1 is withdrawn and temperature read from the thermometer 30. The analyzing procedure can be followed as described above.

FIGS. 12–19 refer to alternative embodiments of the present invention and alternative means of contacting the fecal specimen with the analyzing solution.

Figure 12:
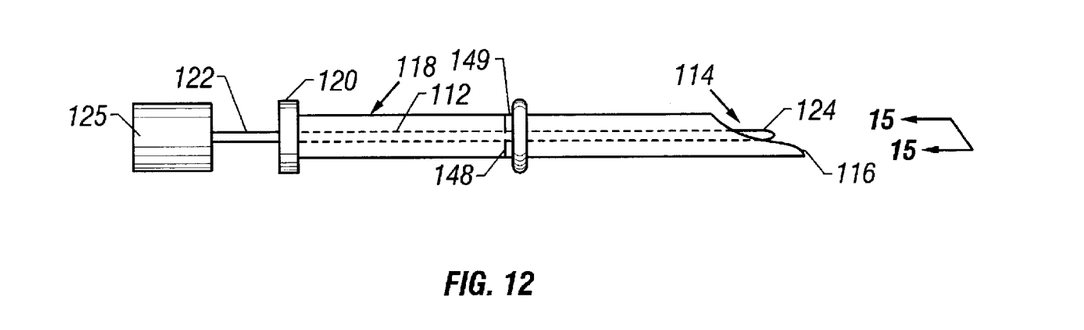
FIG. 12 is a side elevation of an embodiment of the present invention, wherein the sleeve is adapted for insertion into a test tube.
Figure 15:
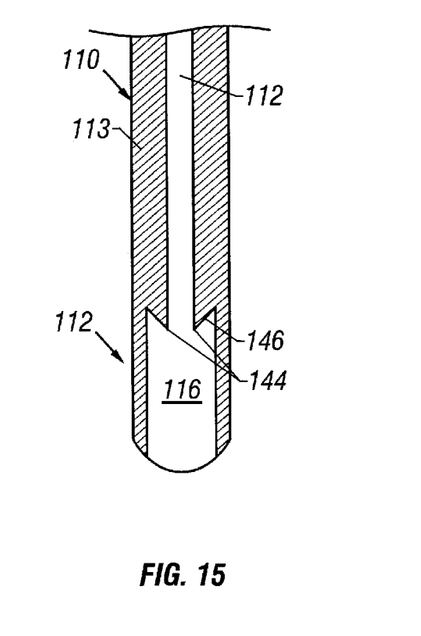
FIG. 15 is an enlarged cross-sectional view of the distal end of the embodiment of FIG. 12 as seen along the lines 15—15.

A sleeve 110, as seen in FIGS. 12 and 15 has an interior bore 112 forming a wall 113 and an exterior surface with a diameter suitable for insertion into the rectum. As mentioned previously the sleeve 110 is preferably an elongated, cylindrical, substantially rigid tube having an appropriate length to gather the fecal specimen. The sleeve has a distal end 114 formed into a scoop 116 and a proximal end 118 preferably including a flange 120 for handling the sleeve 110 and facilitating insertion of the sleeve 110 into the rectum. The scoop 116 shown in greater detail in FIG. 15 preferably has a bevel 144 forming a hollow annular shoulder 146 to facilitate specimen collection and minimize retention of fecal matter on the thermometer as it is withdrawn from the bore 112. The shoulder 146 serves to scrape and collect such fecal material from the surface of the thermometer or thermistor.

In FIG. 12, a body temperature measuring device 122 is inserted into the interior bore 112 so that a temperature measuring end 124 is removably secured adjacent the scoop 116 inside the rectum. Examples of suitable temperature measuring devices include both mercury-type thermometers and electronic devices such as thermocouple and thermistor wires. A thermistor is conveniently employed in this embodiment and has an electrical connection end 125, suitably connected, for example, to a conventional digital display (not shown). While different means previously described can be used to secure the position of the temperature measuring device 122 in the interior bore 112, a preferred securing means is provided by closely dimensioning the diameter of the temperature measuring device 122 (e.g. a thermistor wire) to the diameter of the bore 112.

The sleeve 110 is adapted for analyzing the fecal specimen in the scoop 116 following the fecal sampling procedure. Thus, additional transfer steps are not necessary to conduct many of the common medical tests for which a fecal specimen is necessary (e.g. occult blood test, presence of parasite eggs, and the like). At an approximate mid-position, the sleeve 110 has an exteriorly extending shoulder 126 separating the distal and proximal ends 114, 118. The shoulder 126 is designed to sealably lock the distal end 114 of the sleeve 110 in a test tube or vial 130 (see FIGS. 13–14).

Figure 13:
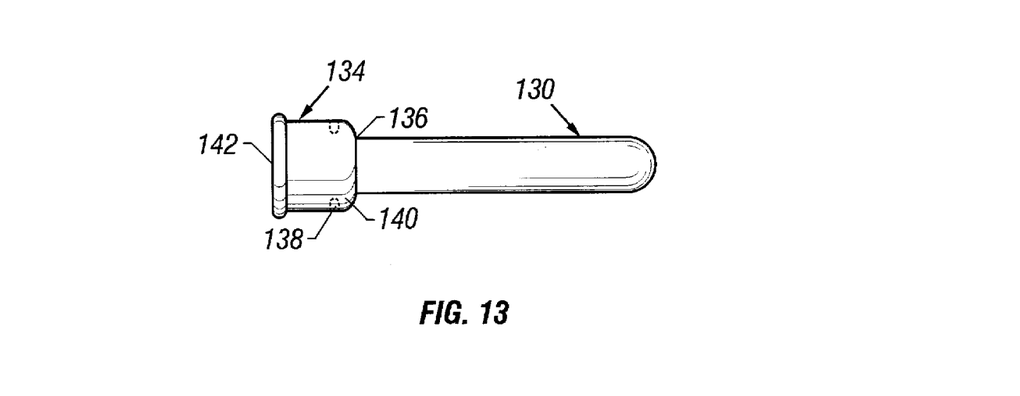
FIG. 13 is a side elevation of the test tube adapted for receiving the embodiment of the present invention shown in FIG. 12.
Figure 14:
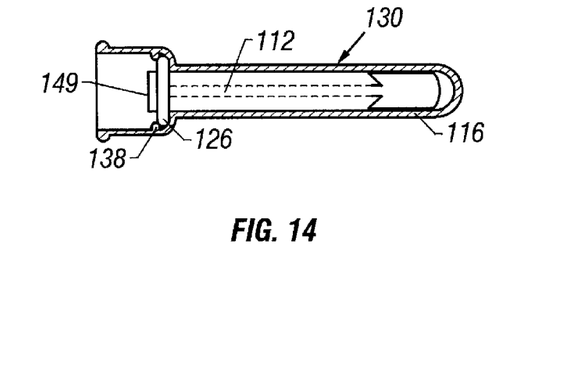
FIG. 14 is a side elevation of the present invention in partial cross-section showing the sleeve of FIG. 12 inserted into the test tube of FIG. 13 with temperature measuring device removed and the proximal end cleaved.

The test tube 130, as seen in FIGS. 13–14, has a lower section 132 for receiving the distal end 114 of the sleeve 110 and an upper section 134 having a larger diameter. An interiorly extending shoulder 138 in the upper test tube section 134 forms a seat 140 at a junction 136 of the upper and lower sections 134, 132. The seat 140 receives the shoulder 126 and locks the distal end 114 of the sleeve 110 in the lower section 132 of the test tube 130. A ring member 142 is attached to a lip on the test tube 130 for increasing the strength of the lip where a stopper (not shown) can be used to seal the contents of the test tube 130.

To enhance the ease of storing and analyzing the fecal specimen once the sleeve 110 containing the fecal specimen is inserted into the test tube 130 and seated therein, the proximal end 118 of the sleeve 110 is preferably cleaved from the distal end 114 (see FIG. 14) by applying hand pressure to the sleeve 110 at a pressure point comprising a scoring 148. The scoring 148 is preferably made in the sleeve 110 just above the shoulder 126 so that proximal end 118 can be conveniently separated from the distal end 114, except, possibly, for a small tab end 149. The tab end 149 is preferably entirely contained in the test tube 130 and is disposed adjacent the interiorly extending shoulder 138.

The test tube 130 is preferably made of a plastic material such as polystyrene, polyethylene or polypropylene, which normally should be the same material as the sleeve 110.

Figure 18:
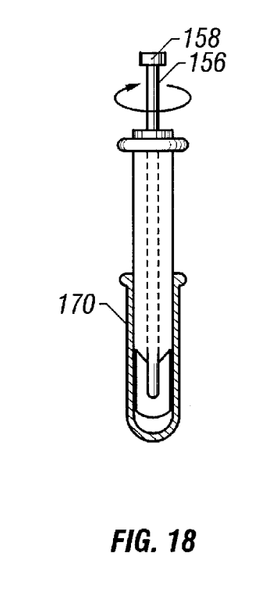
FIG. 18 is a partial cross-sectional view of the present invention showing the sleeve of FIG. 12 inserted into a cap with the temperature measuring device removed, the proximal end cleaved and a manual stirrer inserted into the interior bore.
Figure 19:
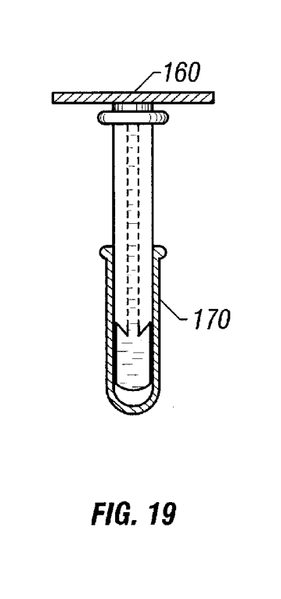
FIG. 19 shows the sleeve and cap of FIG. 18 with the manual stirrer removed and a slide wetted by the meniscus of the mixed analyzing solution.
Figure 20:
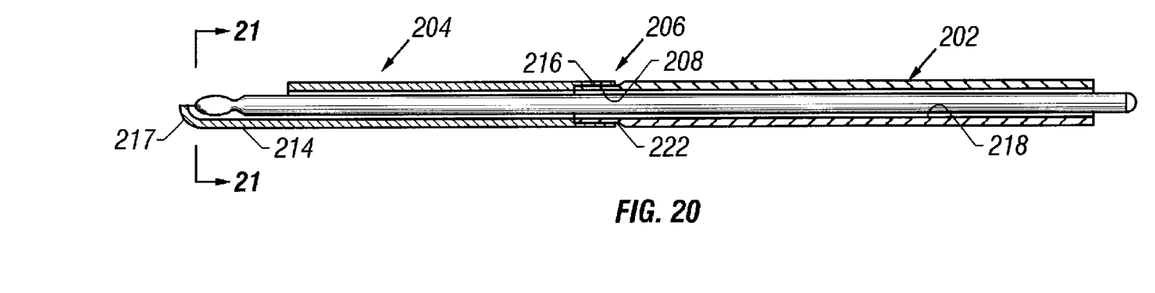
FIG. 20 illustrates another embodiment of the thermometer and sleeve assembly of the present invention.

As an alternative embodiment, the sleeve 110 containing the fecal specimen can be covered with a cap or vial 170 seen in FIGS. 18–19, thus enclosing the region around the specimen for containment of the analyzing solution contacting the fecal specimen. The cap 170 can be made of a rubber such as latex having an appropriate diameter for sealing against the exterior surface of the sleeve 110 to prevent loss of analyzing fluids.

Figure 16:
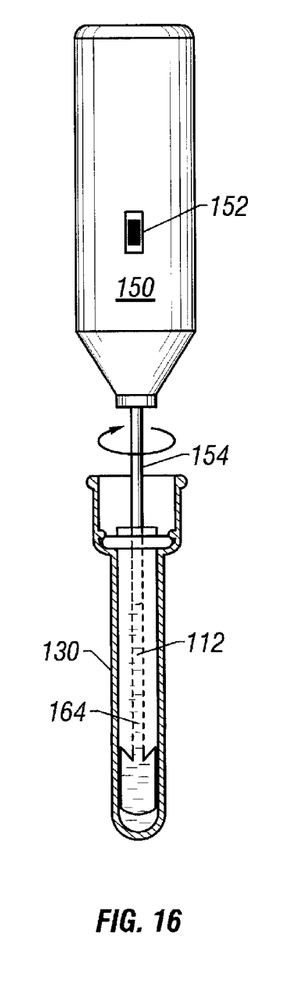
FIG. 16 is a side view, partially in section, of the embodiment seen in FIG. 14 showing an automatic stirrer mixing a fecal specimen in the scoop with an analyzing solution in the test tube.

To analyze the fecal specimen collected in the scoop 116 of the sleeve 110, the specimen is contacted with an appropriate analyzing solution 164. The distal end 114 of the sleeve 110 can be inserted directly into the analyzing solution contained in the test tube or the solution can be added afterwards through the interior bore 112. The proximal end 118 of the sleeve 110 is preferably separated and the fluid/specimen contents of the test tube are mixed. An automatic mixer 150 with an on/off switch 152 comprising a rotating rod 154 is shown in FIG. 16, wherein the stirring rod 154 is inserted into the interior bore 112 of the sleeve 110. Rotation of the rod 154 swirls the liquid contents of the test tube. Alternatively, a manual mixing rod 156 with a handle 158 is seen in FIG. 18.

Figure 17:
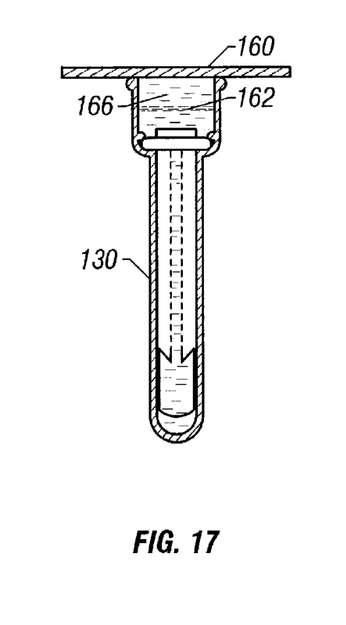
FIG. 17 is a side sectional view of the test tube of FIG. 16 with the stirrer removed and a microscope slide wetted at a meniscus of the mixed analyzing solution.

Following mixing, a microscope slide 160 can be wetted with the liquor 166 to determine presence of ova, parasites and/or bacteria, under a microscope (FIGS. 17 and 19). Generally, the mixing rod 154 or 156 is withdrawn and additional liquid is added, if necessary, by eye-dropper, for example, to increase the liquid level in the test tube 130 (FIG. 17) or the interior bore 112 (FIG. 19) so that the slide can be contacted with an exposed liquid meniscus (not shown). The wetted slide can then be prepared for observation under a microscope. A screen 162 can be installed across the diameter of the test tube upper section 134 if desired to help prevent particles of fecal matter from adhering to the slide 160.

Another preferred embodiment of the present invention is illustrated in FIGS. 20–25. A sleeve 200 comprises a proximal section 202 and a distal section 204 which are joined together at the rabbet joint 206 to form an elongated tube. The proximal section 202 has a generally uniform outside diameter which terminates adjacent the distal section 204 at a thin-walled end 208 having a reduced outside diameter. The section 202 has a generally uniform inside diameter along its length, but can optionally include inward protrusions (not shown) to facilitate frictional engagement of a thermometer or other temperature-measuring device.

Figure 21:
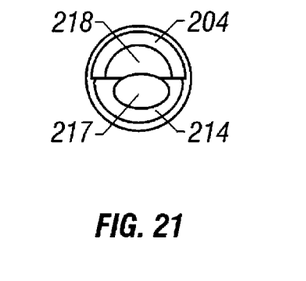
FIG. 21 is an end view of the sleeve of FIG. 20 as seen along the lines 21—21.
Figure 22:
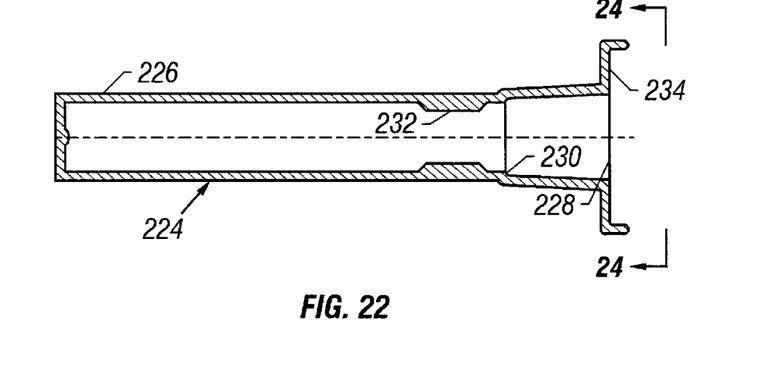
FIG. 22 is a side sectional view of a vial for use with the device of FIGS. 20–21.
Figure 23:
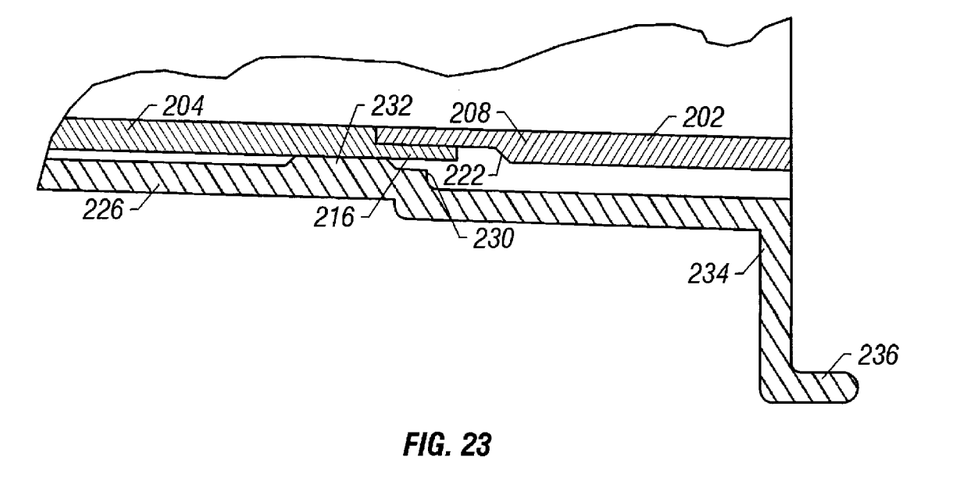
FIG. 23 is an enlarged section of the vial of FIG. 22 after insertion therein of the device of FIGS. 20–21.
Figure 24:
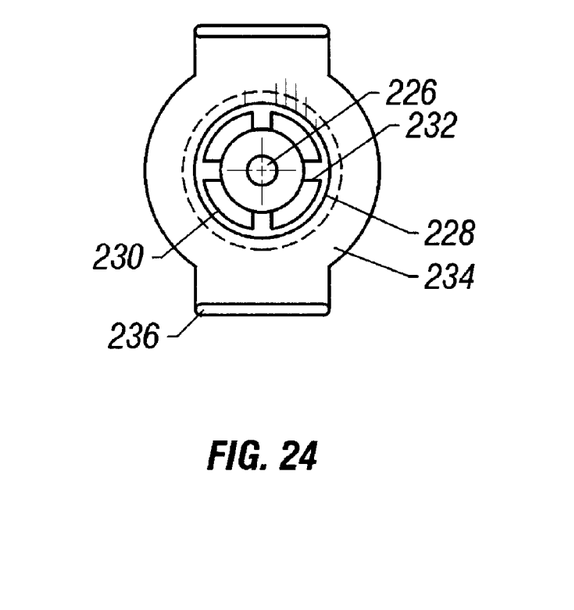
FIG. 24 is an end view of the vial of FIG. 22 as seen along the lines 24—24.

The distal section 204 has a scoop 214 adjacent one end opposite the rabbet joint 206 and a generally uniform outside diameter. A generally uniform inside diameter terminates at a thin-walled end 216 having an enlarged inside diameter. The inside diameter of the end 216 closely matches the outside diameter of the end 208 for frictional, cemented, welded, glued or like engagement in the rabbet joint 206. The scoop 214 is formed by rounding the distal tip 217 and cutting away one side of the section 204 adjacent the tip 217 along a relatively short length of the section 204. As seen in FIG. 21, the tip 217 is cut away to form a longitudinal or axial opening into a longitudinal bore 218 visible from the end perspective to facilitate fecal sampling.

The sections 202 and 204 can be made from a molded thermoplastic such as polyethylene, polypropylene, polystyrene, or the like. The molded sections 202 and 204 are then assembled by inserting the end 208 into the end 216 to form the joint 206. The joint 206 can be held together by friction between the tightly matched diameters, thermal fusion, solvent fusion (e.g. methylene chloride for polystyrene), the use of an adhesive or glue between the opposed surfaces, mechanical coupling devices such as pins or rivets, or the like. All that is required is that the joint 206 hold the sections 202 and 204 together during rectal insertion, specimen sampling and removal.

For specimen sampling with temperature measurement, a thermometer 220 is inserted in proximal section 202 through the bore 218 and into distal section 204 until the thermometer 220 is thermally exposed adjacent the scoop 214. The thermometer 220 preferably has an outside diameter to match the diameter of the bore 218 for frictional engagement thereby, e.g. the thermometer has a slightly longer transverse dimension to be tightly but releasably gripped in the bore 218. The thermometer 220, or other temperature sensing element, can leave sufficient volume in the scoop 214 for the fecal specimen, but can alternately or additionally be withdrawn from the sleeve 200 while the sleeve 200 is held in the rectum or other sampling region. The temperature indication can be read after the thermometer has been inserted for a sufficient time period to reach thermal equilibrium, either visually after withdrawing the thermometer 220 from the rectum, or on a conventional local or remote readout (not shown) in the case of a thermistor or thermocouple, for example, a digital readout. When the thermometer 220 is used, the sleeve 200 can also provide magnification to facilitate the reading by construction from the materials having the appropriate optical properties.

Fecal specimen collection is effected by filling the scoop 214 during rectal insertion and/or by rotation, pivoting or otherwise working the proximal section 202 which is not completely inserted into the rectum to facilitate such manipulation. Leaving a portion of the proximal section 202 uninserted also facilitates removal when specimen collection and/or temperature measurement are completed. As desired, the distal section 204 and/or the rectum can be lubricated as for conventional rectal thermometers, although care should be exercised to avoid blocking or filling the scoop 214 with the lubricant.

Preferably, after thermometer removal, the distal section 204, containing the specimen in the scoop 214, can be separated from the proximal section 202 by breaking along the fracture line 222. The fracture line 222 is created at the thin wall 208 adjacent the termination of the larger outside diameter of the proximal section 202. There is preferably a gap between the end 216 and the end of the outside diameter of the proximal section 202 such that the thin wall 208 is exposed for a longitudinal dimension approximately from 0.5 to 5 times the thickness of the wall 208, more preferably from 1 to 3 wall thicknesses, especially where the material is polystyrene.

A vial 224 can be conveniently used for specimen analysis with the sleeve 200 as shown in FIGS. 22–25. The vial 224 is elongated with a cap 226 at one end and an opening 228 at the other. The cap 226 has a length and diameter sufficient to receive the distal section 204 therein. At a base of the opening 228, a shoulder 230 is preferably formed by a reduction in the inside diameter adjacent the cap 226. A plurality of inwardly extending longitudinal fins 232 are disposed in the cap 226 adjacent to the shoulder 230. A pair of opposed flanges 234 extend radially outwardly from adjacent the opening 228 to lips 236. The vial 224 is conveniently molded from the same material as the sleeve 200.

Figure 25:
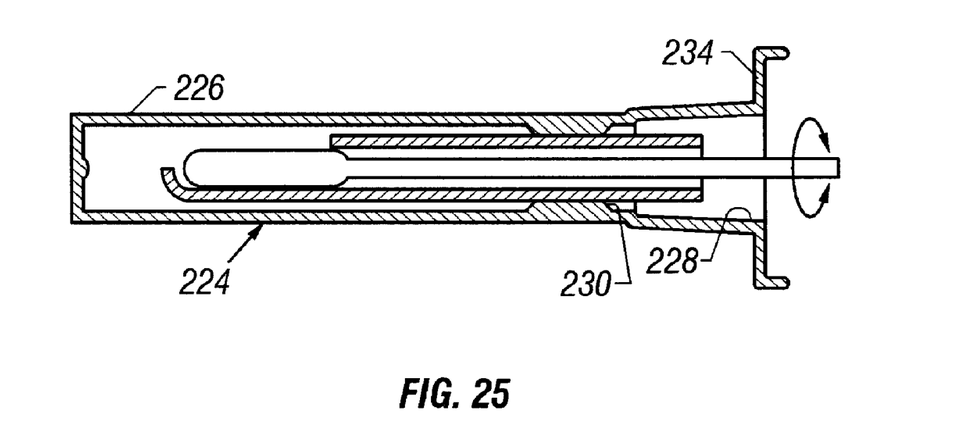
FIG. 25 is a side sectional view of the distal end of the device of FIGS. 20–21 secured in the vial of FIGS. 22–24 for mixing the fecal specimen with the analyzing solution.

The vial 224 receives the sleeve 200, and the distal section 204 is forced into the cap 226 so that the fins 232 tightly engage the outside diameter of the distal section 204 containing the fecal specimen in the scoop 214. Then secured in the vial 224 by friction, the sleeve 200 is bent by twisting the proximal section 202 against the vial 224, to induce fracture of the sleeve 200 at the fracture line 222 comprising the thin wall 208 between the end 216 and the larger outside diameter of the proximal section 202. Then, with the proximal section 202 removed and the distal section 204 retained in the vial 224, the fecal specimen can be examined, as described above, for parasites, ova, viruses, yeast or bacteria, or the like, using the opposed flanges 234 and lips 236 to hold the microscope slide. If desired, a paddle 240 can be inserted into the distal section 204 as shown in FIG. 25, and manipulated, by rotation and/or reciprocation, for example, manually or by an electrically powered, hand-held driver (not shown) to mix the fecal specimen with reagent or solvent fluid in the cap 226.

The fecal specimen sampling sleeve 200 can also be used for fecal sampling and analysis where the temperature measurement is not required, for example, by rectal insertion, and also from patient stools as in bedpans or fecal specimen cups. In this mode of use, the sleeve 200 sans thermometer is grasped by the proximal section 202 and the distal section 204 is inserted in the stool or other fecal material to be sampled to collect a fecal specimen in the s scoop 214. The distal end 202 is then inserted into the vial 226, locked by the fins 232 and the proximal end 202 broken off. The fecal specimen in the scoop 214 is thus secured in the vial 224 for fecal analysis. The analysis can be done immediately as described above, or the vial 224 can be optionally sealed, stoppered or otherwise plugged adjacent the flanges 234 for shipment to an analysis lab and/or later analysis.

Test reagent, preservative or the like can also be pre-placed in the bottom of the cap 226, e.g. in a vial or sealed by a membrane (not shown) which is broken or pierced by the scoop 214 to release the reagent or preservative when the sleeve is inserted into the vial 224.

The foregoing description of the invention is illustrative and explanatory thereof. Various changes in the materials, apparatus, and particular parts employed will occur to those skilled in the art. It is intended that all such variations within the scope and spirit of the appended claims be embraced thereby.

What is claimed is:

1. A device useful with a temperature measuring device for simultaneously sampling a fecal specimen and measuring rectal temperature, comprising:

(a) a rigid and elongated disposable tubular sleeve having open proximal and distal ends, said distal end having rounded edges adapted for rectal insertion and at least partially cut away longitudinally and transversely to form an open-ended scoop for collecting and containing a fecal specimen;

(b) an interior bore formed through said sleeve adapted for removably inserting and frictionally engaging the temperature measuring device therein having a temperature sensing end thermally exposed adjacent said scoop for concurrently measuring rectal temperature; and (c) an enclosure adapted to be sealably secured around said scoop for containing an analyzing solution in fluid contact with said fecal specimen in said scoop.

2. The device of claim 1, wherein said enclosure comprises a vial having an interior seat for frictional engagement with an exterior surface of said sleeve and a cap for containment of said solution.

3. The device of claim 1, wherein said enclosure comprises a cap sealable around said scoop.

4. The device of claim 1, wherein said sleeve includes a mechanically weakened section formed between said proximal and distal ends for cleaving said proximal end from said distal end disposed in said enclosure.

5. The device of claim 1, further comprising a stirring rod receivable by said interior bore and rotatable therein for mixing said fecal specimen in said scoop with said analyzing solution in said enclosure.

6. A kit useful with a temperature measuring device for rectal temperature measurement and for fecal sampling and analysis, comprising:

(a) an elongated rigid disposable tubular sleeve having a generally smooth exterior profile and proximal and distal ends;

(b) a scoop adapted for rectal insertion and fecal sampling formed in said distal end;

(c) a longitudinal bore formed through said sleeve for releasably receiving the temperature measuring device therein;

(d) a thin walled fracture section of the sleeve formed between said proximal and distal ends;

(e) a vial having opposite open and closed ends and an interior engagement surface adapted to receive the scoop and distal end of the sleeve in frictional engagement between the exterior surface of the sleeve and the interior engagement surface of the vial, wherein the scoop and distal end are longitudinally disposed between the opposite ends of the vial.

7. The kit of claim 6, wherein the interior engagement surface of the vial comprises a plurality of inwardly protruding longitudinal fins.

8. The kit of claim 6, comprising a flange formed adjacent the open end of the vial for mounting a microscope slide thereon.

9. The kit of claim 6, further comprising a stirrer having a paddle attached to a longitudinal handle, adapted for insertion into the longitudinal bore of the distal section secured in the vial separated from the proximal section adjacent the fracture section, and for agitation of the fluid in the vial by the paddle adjacent the scoop by manipulation of the handle extending out of the open end of the vial.

10. The kit of claim 9, further comprising a hand-held appliance for mechanically rotating said handle.

11. The kit of claim 6, further comprising a temperature measuring device adapted for releasable engagement in said longitudinal bore.

12. A method for sampling a fecal specimen and optionally measuring rectal temperature with the device of claim 1, comprising the steps of:

(a) inserting said sleeve into the rectum;

(b) sampling said fecal specimen;

(c) optionally measuring said temperature with the temperature measuring device inserted in the interior bore;

(d) withdrawing the device of claim 1 from the rectum;

(e) sealably securing said enclosure around said scoop; and (f) contacting said fecal specimen with an analyzing fluid in the enclosure.

13. The method of claim 12, wherein said inserting and sampling steps are done with said temperature measuring device frictionally engaged in said interior bore, and further comprising the steps of removing said temperature measuring device from said sleeve, contacting said fecal specimen in said scoop with an analyzing solution and reading a test result.

14. The method of claim 13, wherein said contacting step comprises enclosing said scoop with a vial and mixing said fecal specimen with said analyzing solution.

15. The method of claim 14, wherein said vial has opposite open and closed ends and an interior engagement surface adapted to receive the scoop and distal end of the sleeve in frictional engagement between the exterior surface of the sleeve and the interior engagement surface of the vial, wherein the scoop and distal end are longitudinally disposed between the opposite ends of the vial.

16. The method of claim 15, wherein said mixing step includes manipulating a stirring rod inserted into said interior bore.

17. The method of claim 15, further comprising the steps of cleaving said distal end of said sleeve from said proximal end following said securing step (e) and wetting a microscope slide, removably mounted on a flange formed adjacent said open end of the vial, with a meniscus of the test solution following said mixing step.

* * * * *